US008815963B1

(12) United States Patent
Caram et al.

(10) Patent No.: US 8,815,963 B1
(45) Date of Patent: Aug. 26, 2014

(54) CATALYST COMPOSITION FORMULATED FOR SYNTHESIS OF ALCOHOLS AND METHOD OF PREPARING THE SAME

(71) Applicants: Auxilium Green, LLC, Bedminster, NJ (US); Lehigh University

(72) Inventors: Hugo S. Caram, Allentown, PA (US); Ranjan K. Sahoo, Bethlehem, PA (US); Richard G. Herman, Whiteall, PA (US); Divyanshu R. Acharya, Bridgewater, NJ (US)

(73) Assignees: Auxilium Green, LLC, Bedminster, NJ (US); Lehigh University, Bethlehem, PA (US)

( * ) Notice: Subject to any disclaimer, the term of this patent is extended or adjusted under 35 U.S.C. 154(b) by 0 days.

(21) Appl. No.: 14/070,768

(22) Filed: Nov. 4, 2013

(51) Int. Cl.
*C07C 27/22* (2006.01)
*B01J 27/051* (2006.01)
*C07C 29/153* (2006.01)

(52) U.S. Cl.
CPC .............. *B01J 27/051* (2013.01); *C07C 29/153* (2013.01)
USPC .......................................... 518/714; 502/220

(58) Field of Classification Search
CPC .... C07C 29/153; C07C 1/043; C07C 1/0445; B01J 37/20; B01J 23/85; B01J 23/88
USPC ............................ 518/715, 714; 502/220, 221
See application file for complete search history.

(56) References Cited

U.S. PATENT DOCUMENTS

| | | | |
|---|---|---|---|
| 4,675,344 A | 6/1987 | Conway et al. ............... 518/714 |
| 4,749,724 A * | 6/1988 | Quarderer et al. ........... 518/714 |
| 4,752,622 A | 6/1988 | Stevens ....................... 518/714 |
| 4,752,623 A | 6/1988 | Stevens et al. ............... 518/714 |
| 4,825,013 A | 4/1989 | Quarderer et al. ........ 568/902.2 |
| 4,831,060 A | 5/1989 | Stevens et al. ............... 518/714 |
| 4,882,360 A | 11/1989 | Stevens ....................... 518/714 |
| 4,994,498 A | 2/1991 | Kinkade ....................... 518/714 |
| 5,102,845 A | 4/1992 | Kinkade ....................... 502/170 |
| 5,449,655 A * | 9/1995 | Albers et al. ................. 502/185 |
| 7,199,276 B2 | 4/2007 | Sher et al. .................... 585/640 |
| 7,288,689 B2 | 10/2007 | Janssen et al. ............... 585/640 |
| 7,384,987 B2 | 6/2008 | Iordache-Cazana et al. . 518/715 |
| 7,923,405 B2 | 4/2011 | Kharas et al. ................ 502/216 |
| 8,110,522 B2 | 2/2012 | Meitzner et al. ............. 502/220 |
| 8,273,138 B2 | 9/2012 | Bauldreay et al. ............ 44/307 |
| 8,344,184 B2 | 1/2013 | Stites ........................... 568/840 |
| 8,354,357 B2 | 1/2013 | Kharas et al. ................ 502/216 |
| 8,367,882 B2 | 2/2013 | Cortright et al. ............. 585/240 |
| 8,399,715 B2 | 3/2013 | Kharas et al. ................ 568/840 |
| 2009/0156393 A1 | 6/2009 | Kharas ......................... 502/164 |
| 2010/0210741 A1 | 8/2010 | Kharas ......................... 518/714 |
| 2012/0065279 A1 | 3/2012 | Su ................................ 518/714 |
| 2013/0245137 A1 * | 9/2013 | Jones et al. ................... 518/714 |

FOREIGN PATENT DOCUMENTS

| | | | |
|---|---|---|---|
| EP | 0119609 A1 | 9/1984 | .............. C07C 29/15 |
| EP | 0149255 A2 | 7/1985 | .............. C07C 29/15 |
| EP | 0149256 A2 | 7/1985 | .............. C07C 29/16 |
| EP | 0170973 A2 | 2/1986 | .............. C07C 29/15 |

OTHER PUBLICATIONS

J.M.Christensen, P.M. Mortensen, R. Trane, P.A. Jensen, A.D. Jensen;"Effects of $H_2S$ and process conditions in the synthesis of mixed alcohols from syngas over alkali promoted cobalt-molybdenum sulfide"; Applied Catalysis A: General 366 (2009); pp. 29-43.
Jamshid Iranmahboob, Donald O. Hill, Hossein Toghiani; "$K_2CO_3$/Co-$MoS_2$/clay catalyst for synthesis of alcohol: influence of potassium and cobalt"; Applied Catalysis A: General 231 (2002); pp. 99-108.
Jamshid Iranmahboob, and Donald O. Hill; "Alcohol synthesis from syngas over $K_2CO_3$/CoS/$MoS_2$ on activated carbon"; Catalysis Letters, vol. 78, Nos. 1-4, Mar. 2002; pp. 49-55.
Jamshid Iranmahboob, Hossein Toghiani, Donald O. Hill, Farhad Nadim; "The influence of clay on $K_2CO_3$/Co-$MoS_2$ catalyst in the production of higher alcohol fuel"; Fuel Processing Technology 79 (2002); pp. 71-75.
Venkateswara Rao Surisetty, A. Tavasoli, A.K. Dalai; "Synthesis of higher alcohols from syngas over alkali promoted $MoS_2$ catalysts supported on multi-walled carbon nanotubes"; Applied Catalysis A: General 365 (2009); pp. 243-251.

* cited by examiner

*Primary Examiner* — Fereydoun G Sajjadi
*Assistant Examiner* — Mark Luderer
(74) *Attorney, Agent, or Firm* — Watov & Kipnes, P.C.; Kenneth Watov

(57) ABSTRACT

A catalyst composition includes an active material having a molybdenum- and sulfur-containing substance impregnated with an effective amount of cesium sufficient to promote synthesis of an alcohol, optionally carried on an inert support, wherein the active material is at least substantially free of a transition metal. The present invention is further directed to methods of preparing and using the same.

50 Claims, 8 Drawing Sheets

CATALYST COMPOSITION FORMULATED FOR SYNTHESIS OF ALCOHOLS AND METHOD OF PREPARING THE SAME

FIELD OF THE INVENTION

The present invention relates generally to renewable energy production, and more particularly a catalyst composition formulated for synthesizing ethanol and higher alcohols from synthesis gas (syngas).

BACKGROUND OF THE INVENTION

For decades, alcohols have long been used as renewable fuels and fuel additives such as, for example, octane boosters in gasoline formulated fuels. In 2011, world ethanol production for fuels reached 22.36 billion US gallons with the United States as the top producer at 13.9 billion US gallons. Alcohol-based additives including methanol (derived from natural gas), and ethanol (derived from bio-mass sources) offer relatively high blending octane numbers, competitive pricing and ample availability.

Energy-volume densities of alcohols are generally much lower than gasoline. For example, the energy-volume density of methanol is about 18.6 MJ/L, while gasoline is about 34 MJ/L. Although methanol's energy-volume density is relatively low, the energy-volume density of alcohols increases with increasing molecular weight of the particular alcohol. Higher alcohols such as, for example, ethanol and butanol have energy-volume densities of about 24 MJ/L and 29.2 MJ/L, respectively. If adequate supplies of ethanol, as well as mixtures of higher alcohols, can be made available, such higher alcohols can be utilized extensively on a wider scale, particularly as an alternative fuel, as well as booster additives for both octane and cetane fuels.

Since the early $20^{th}$ century, catalysts have been formulated to produce mixtures of methanol and higher alcohols from syngas (a gas mixture composed of hydrogen and carbon monoxide). Certain catalysts formulated for synthesizing hydrocarbons from syngas were later discovered by Fischer and Tropsch (FT) to produce linear alcohols as by-products when impregnated with alkali impurities. This discovery eventually led to the development of other FT catalysts and alkali-doped zinc oxide/chromium (III) oxide catalysts capable of higher alcohol synthesis (HAS). During the late 1940's, the discovery of high yield oil fields diminished commercial interest in synthesis of alcohol from syngas.

Recently, in the face of rising crude oil costs and the nation's increasing reliance on foreign sources of oil, the Energy Independence and Security Act of 2007 was passed requiring the total amount of renewable fuels added to gasoline formulations be raised to 36 billion US gallons by 2022. These considerations have resulted in renewed interest and research in the synthesis of higher alcohols (HA) including ethanol.

Thermochemical conversion of biomass to ethanol and higher alcohols seems to offer an attractive and promising source of renewable energy. This process includes converting biomass into syngas, and then catalytically converting syngas to ethanol and other higher alcohols. Plentiful biomass, particularly agricultural and forest refuse, municipal solid waste, landfill gas, and the like, represent a potential source of syngas. Such biomass-based sources of renewable energy are expected to play an increasingly important role in the synthesis of clean, sustainable fuels and fuel additives.

Accordingly, there is a need in the art to develop a catalyst composition and method of using the same with enhanced productivity and selectivity for synthesis of an alcohol from synthesis gas. There is also a need for a catalyst composition and method of using the same characterized by long term stability, reduced water formation and other undesirable by-products, and being relatively easy to make and implement at lower costs.

SUMMARY OF THE INVENTION

The present invention relates generally to a catalyst composition and method of using the same for promoting the synthesis of an alcohol, preferably ethanol and higher alcohols (HA), from synthesis gas or syngas. The present invention also relates to a method of preparing the catalyst composition in a manner that reduces production cost, while ensuring improved quality and consistency.

The catalyst composition of the present invention exhibits improved properties such as long term stability with minimal loss of performance or mechanical integrity, while suffering no loss of sulfur during synthesis operation. Since sulfur in the present invention remains conserved throughout the synthesis operation, the catalyst composition does not require continuous or periodic re-activation through re-sulfidation. This eliminates sulfur contaminants in the product alcohols stream. The catalyst composition of the present invention is further characterized by reduced formation of water and other undesirable by-products, thereby realizing additional cost savings.

Generally, the catalyst composition includes an active material having a molybdenum- and sulfur-containing substance impregnated with an effective amount of cesium sufficient to promote synthesis of alcohol from syngas, wherein the active material is at least substantially free of a transition metal. The molybdenum- and sulfur-containing substance is preferably molybdenum sulfide. In a particular embodiment of the present invention, the active material is carried on an inert support. The inert support is preferably selected from an inert porous material having a relatively high surface area and should be neutral or basic or should be rendered neutral or basic upon alkali, such as cesium or potassium impregnation, for example, activated carbon.

In one aspect of the present invention, there is provided a catalyst composition, comprising an active material having a molybdenum- and sulfur-containing substance impregnated with an effective amount of cesium sufficient to promote synthesis of an alcohol, carried on an inert support, wherein the active material is at least substantially free of a transition metal.

In another aspect of the present invention, there is provided a method of preparing a catalyst composition, including the steps of:

reacting crystalline molybdenum oxide with a sulfur source to produce a molybdenum- and sulfur-containing substance at least substantially free of a transition metal; and distributing cesium uniformly through the molybdenum- and sulfur-containing substance.

In another aspect of the present invention, there is provided a method of promoting synthesis of an alcohol from synthesis gas or syngas, including the steps of:

acquiring a catalyst composition comprising an active material having a molybdenum- and sulfur-containing substance impregnated with an effective amount of cesium sufficient to promote synthesis of an alcohol, carried on an inert support, wherein the active material is at least substantially free of a transition metal; and contacting a mixture of hydrogen and carbon monoxide to the catalyst composition under suitable conditions to yield an alcohol.

BRIEF DESCRIPTION OF THE DRAWINGS

The following drawings are illustrative of embodiments of the invention and are not intended to limit the invention as encompassed by the claims forming part of the invention, wherein like items are identified by the same reference designation.

DETAILED DESCRIPTION OF THE INVENTION

Figure 1:
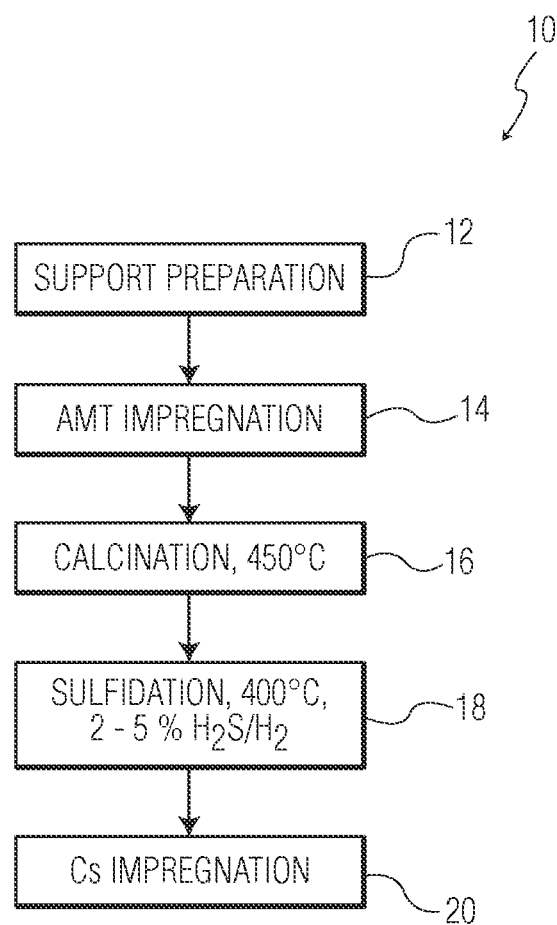
FIG. 1 is a flowchart illustrating a method of preparing a catalyst composition in accordance with one embodiment of the present invention.

The present invention is generally directed to a catalyst composition and method of using the same for promoting synthesis of an alcohol, preferably ethanol and higher alcohols (HA), from synthesis gas or syngas. The present invention also relates to a method of preparing the catalyst composition in a manner that reduces production cost, while ensuring improved quality and consistency. The catalyst composition of the present invention exhibits improved properties such as long term stability with minimal loss of performance or mechanical integrity, while suffering no loss of sulfur during synthesis operation. Since sulfur in the present invention remains conserved throughout the synthesis operation, the catalyst composition does not require continuous or periodic re-activation through re-sulfidation. This eliminates sulfur contaminants in the product alcohols stream. The catalyst composition of the present invention is further characterized by reduced formation of water and other undesirable by-products, thus realizing additional cost savings.

The terms "synthesis gas" or "syngas" refer to a gas mixture of hydrogen and carbon monoxide formulated as a starting material for conversion into alcohols via catalytic processes of the present invention. Syngas can be produced from any hydrocarbon feedstock including natural gas, residual oil, coal, petroleum coke, naptha, and biomass.

The term "catalyst composition" refers to a composition comprising an active material exhibiting catalytic activity suitable for catalytically promoting a desired reaction. The catalyst composition of the present invention can either be in an inactivated state or an activated state when exposed to conditions that make it more suitable for its intended purpose, which in the present invention relates to the conversion of syngas to alcohols.

The term "higher alcohols" refer to alcohols have at least 2 carbon atoms, preferably 2 to 12 carbon atoms. Examples of higher alcohols include ethanol, propanol, butanol, and the like, and all known isomers of such compounds.

Generally, the catalyst composition includes an active material having a molybdenum- and sulfur-containing substance impregnated with an effective amount of cesium sufficient to promote synthesis of alcohol from syngas, wherein the active material is at least substantially free of a transition metal, including, but not limited to, cobalt and nickel. The present catalyst composition exhibits relatively high selectivity towards production of alcohols. The presence of cesium in the active material serves to suppress synthesis of undesirable hydrocarbons, while promoting synthesis of ethanol and higher alcohols. An example of a suitable molybdenum- and sulfur-containing substance includes, but is not limited to, molybdenum sulfide.

In one embodiment of the present invention, the active material of the catalyst composition is present in amount of from about 5 wt % to 70 wt %, based on the total weight of the composition, preferably from about 25 wt % to 35 wt %.

In a preferred embodiment of the present invention, the catalyst composition of the present invention includes a cesium amount of at least 0.1 wt %, based on the total weight of the composition, preferably from about 2 wt % to 30 wt %, and more preferably from about 10 wt % to 15 wt %. The present catalyst composition further includes a cesium to molybdenum mass ratio of at least 0.1, preferably from about 0.5 to 3, and more preferably about 1.

In a further embodiment of the present invention, the catalyst composition comprises an active material having a molybdenum- and sulfur-containing substance impregnated with an effective amount of cesium sufficient to promote synthesis of alcohol from syngas, carried on or affixed to an inert support. The active material can be carried on or affixed to the inert support through any suitable means as known in the art, including but not limited to, impregnation and co-precipitation.

In one embodiment of the present invention, the inert support is composed of a thermally stable material capable of enduring conditions under which the active material is subjected to during activation and catalyst activity. The inert support accelerates distribution of the syngas thereby enhancing contact of the syngas to the active material, while maintaining the mechanical integrity of the active material. Accordingly, the catalytic activity and selectivity of the active material is enhanced for greater throughput and improved synthesis of ethanol and higher alcohols with minimal quantity of side products formed, e.g. hydrocarbons. The inclusion of the inert support further minimizes formation of hot spots due to uneven distribution of the active material that may occur in a given reactor.

In one embodiment of the present invention, the inert support is preferably selected from an inert porous material having a relatively high surface area and should be neutral or basic or should be rendered neutral or basic upon alkali, such as cesium or potassium impregnation. In one embodiment of the present invention, the inert support includes a surface area of at least 850 m²/g, and preferably from about 850 m²/g to 1350 m²/g. The inert support is present in an amount of from about at least 30 wt % based on the total weight of the composition, and preferably from about 65 wt % to 75 wt %. Suitable examples of inert porous materials include, but are not limited to, activated carbon, alumina, silica, magnesium oxide, zirconium dioxide, and niobium pentoxide. A preferred inert support material is activated carbon.

In one embodiment of the present invention, the catalyst composition of the present invention can be further characterized as having an alcohol synthesis of at least 80 g/kg catalyst/hr (that is, 80 grams of alcohol per kilogram of catalyst per hour), and preferably from about 80 g/kg catalyst/hr to 281 g/kg catalyst/hr. In another embodiment of the present invention, the present catalyst composition can further include alcohols selectivity of at least 70%, and preferably from about 70% to 90%. The present catalyst composition can further exhibit a carbon monoxide conversion of at least 7%, and preferably from about 7% to 25%, and synthesize alcohol with an ethanol to methanol weight ratio of from about 0.4 to 0.9, and preferably 0.45 to 0.75. It is noted that the aforesaid characterization of the invention are not meant to be limiting and is merely illustrative of test results obtained by the Inventors, which results may vary depending on the reaction conditions, the reactants used, the amounts of the reactants, and the like.

As used herein, the term "alcohol selectivity" refers to the percent by weight of total alcohols in the product output on carbon dioxide free basis as represented by Equation 1 provided below. As used herein, the term "carbon monoxide conversion" refers to the percentage of carbon monoxide reactant converted into products, including carbon dioxide as represented by Equation 2 provided below. Carbon monoxide conversion measures the amount of carbon monoxide reacted and converted into products, whereas alcohols selectivity measure the distribution of alcohols in the alcohol and hydrocarbon products.

$$Alcohols_{selectivity} = \frac{\Sigma(g/kgcat/hr)_{Alcohols}}{\Sigma(g/kgcat/hr)_{Alcohols} + \Sigma(g/kgcat/hr)_{hydrocarbons}} \times 100 \quad (Eq. 1)$$

$$CO_{conversion} = \frac{CO_{in} - CO_{out}}{CO_{in}} \times 100 \quad (Eq. 2)$$

The present invention will now be described for preparing the catalyst composition. The following description by no means limits the scope and spirit of the present invention.

In one embodiment of the present invention, there is provided a method of preparing a catalyst composition, including the steps of reacting crystalline molybdenum oxide with a sulfur source to produce a molybdenum- and sulfur-containing substance, wherein the molybdenum- and sulfur-containing substance is at least substantially free of a transition metal, and distributing cesium uniformly through the molybdenum- and sulfur-containing substance.

In a preferred embodiment of the present invention, the method of preparing the present catalyst composition may further include forming the crystalline molybdenum (IV) oxide, preferably on an inert support, from a molybdenum oxide precursor selected, for example, from ammonium molybdate tetrahydrate, molybdenum acetylacetonate, and ammonium molybdate salt prepared by mixing molybdic acid in ammonia solution. The supported molybdenum oxide precursor is then converted into crystalline molybdenum oxide via thermal decomposition.

The crystalline molybdenum oxide is preferably formed on an inert support selected from, for example, activated carbon, by impregnating the inert support with the molybdenum oxide precursor, and calcining the precursor at an elevated temperature of from about 400° C. to 550° C., preferably about 450° C., for a sufficient time of at least three hours. The inert support can be impregnated with the molybdenum oxide precursor via a suitable method such as, for example, a rotary evaporation process, to achieve a molybdenum loading of from about 10 wt % to 18 wt % based on the total weight of the impregnated inert support.

Prior to impregnating the inert support, the inert support may be washed with an acid solution such as, for example, nitric acid, acetic acid, formic acid, sulfuric acid, or the like, for one or more times to ensure removal of any contaminants such as, for example, metals.

Once the crystalline molybdenum (IV) oxide is formed, a sulfur source such as, for example, hydrogen sulfide is placed in contact with crystalline molybdenum (IV) oxide to initiate a sulfidation reaction at a reaction temperature of from about 250° C. to 450° C., and preferably about 400° C., until full sulfidation is achieved to yield a molybdenum- and sulfur-containing substance such as, for example, molybdenum sulfide. The resulting product is then treated to remove any hydrogen sulfide physically adsorbed. This can be achieved by passing and purging an inert gas therethrough to strip away any remnant of hydrogen sulfide.

In a particular embodiment of the present invention, the distribution of cesium uniformly through the molybdenum- and sulfur-containing substance can be achieved by impregnating it with a solution of a cesium-containing compound such as, for example, cesium formate, via a suitable method such as, for example, a rotary evaporation process, and drying the impregnated molybdenum- and sulfur-containing substance under an inert atmosphere. The amount of the cesium-containing compound solution applied is preferably selected to achieve a cesium to molybdenum mass ratio of at least 0.1, preferably from about 0.5 to 3 and more preferably about 1.

Referring to FIG. 1, a flowchart 10 is shown detailing a method of preparing the present catalyst composition in accordance with a particular embodiment of the present invention. In step 12, an inert support is prepared by cutting and sieving extruded activated carbon (AC) to yield cylindrical AC particles ranging in size of from about 2.36 mm to 4 mm. Commercial grade virgin AC can be readily obtained from several suppliers such as, for example, Calgon Carbon Corporation of Pittsburgh, Pa., Cabot Norit Americas Inc. of Marshall, Tex, and Siemens Water Technologies of Alpharetta, Ga.

The cut, sieved AC particles are washed by soaking in an aqueous acid solution such as, for example, 1.0 M nitric acid ($HNO_3$) solution, for about 10 minutes and then filtered. The acid wash is repeated about three times. After the final acid wash, the AC particles are rinsed in excess amounts of deionized water to remove any metal impurities that may be present. The AC particles are then vacuum dried overnight at about 70° C.

In step 14, the cut, cleaned and dried AC particles are impregnated with an aqueous solution of ammonium molybdate tetrahydrate (AMT) using a solution feed rate of about 10 to 15 mL/hr in a rotary evaporator to uniformly distribute the solution in the AC particles in a manner similar to a spray drying technique. The AMT solution was prepared by dissolving 30 g of AMT in 100 ml deionized water. AMT obtained complied with registry number CAS No. 12054-85-2 as referenced by the Chemical Abstracts Service.

The tumbling AC particles are preferably maintained at a temperature of about 70° C. via a heated fluid bath of the rotary evaporator. The mass of ammonium molybdate tetrahydrate is selected to achieve a molybdenum (Mo) loading of from about 10 wt % to 18 wt %. It is noted that since the AMT solution is highly unstable at high temperature, preheating of the AMT solution should be avoided. Following impregnation, the impregnated AC particles are vacuum dried overnight at about 70° C.

In step 16, the dried, impregnated AC particles are calcined at an elevated temperature of about 450° C. in a quartz tube reactor for about 3 to 20 hours, depending on the size of the calcining batch. A tube reactor composed of quartz is selected due to its low chemical reactivity with $NH_3$ and $H_2O$ produced during calcination/sulfidation, and with $H_2S$ used as a starting material. An inert atmosphere is preferably maintained by passing an inert gas such as, for example, nitrogen ($N_2$), through the tube reactor during calcination.

Figure 2:
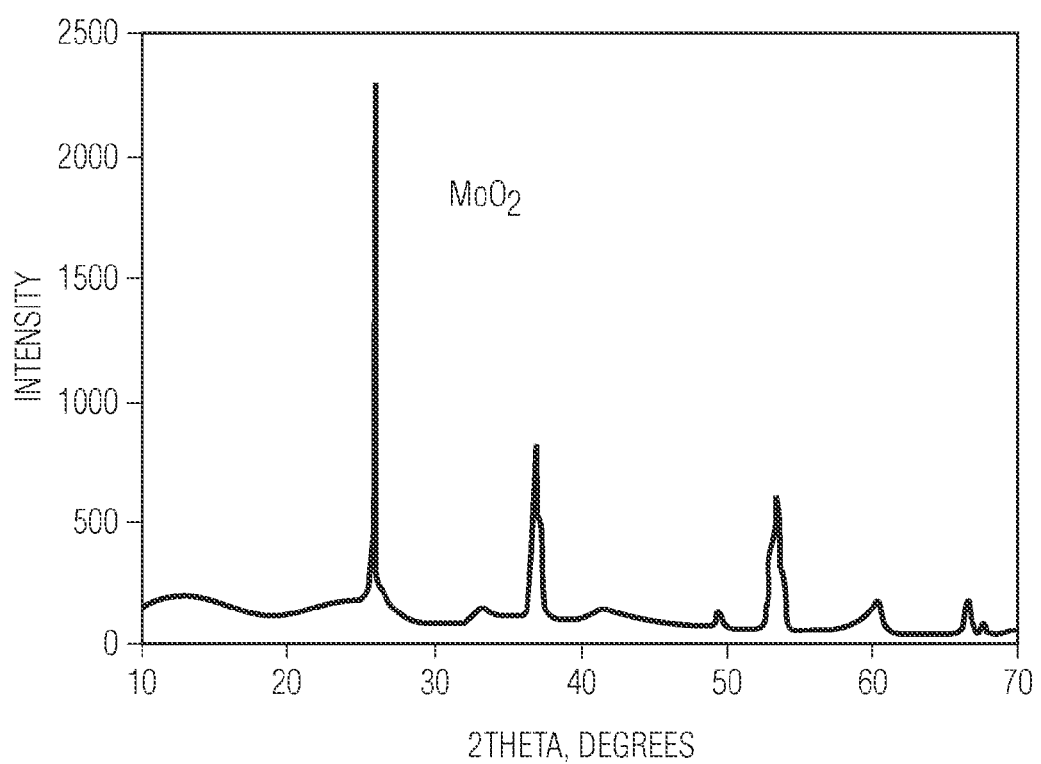
FIG. 2 is a graph plot of an X-ray diffraction pattern of a precursor of the catalyst composition in accordance with one embodiment of the present invention.

Heating is employed using a 6° C. to 7° C./min ramp and the resulting calcined product in the form of pellets is allowed to cool naturally. An X-ray powder diffraction (XRD) pattern of the calcined product is shown in FIG. 2. The resulting calcined product contains crystalline molybdenum (IV) oxide ($MoO_2$). The highly dispersed ammonium molybdate tetrahydrate was thermally decomposed on the porous, high surface area, activated carbon support to yield crystalline $MoO_2$. Following calcination, the pellets are stored under an inert gas atmosphere such as, for example, nitrogen ($N_2$).

In step 18, the pellets composed of $MoO_2$/AC are heated to a temperature of about 400° C. with a 6° C. to 7° C./min ramp under flowing inert gas (e.g., nitrogen) in a quartz tube reactor. The $MoO_2$/AC pellets are sulfidized at about 400° C. under flowing 2% to 5% hydrogen sulfide ($H_2S$) in hydrogen ($H_2$) at a flow rate of about 100 mL/min. Since water vapor is a product of sulfidation of $MoO_3$ or $MoO_2$, the sulfidation process can be monitored by measuring the water content of the gas flow exiting the reactor using gas chromatography. The completion of the sulfidation processing can be determined by observing the presence of water at the outlet of the reactor.

Figure 3:
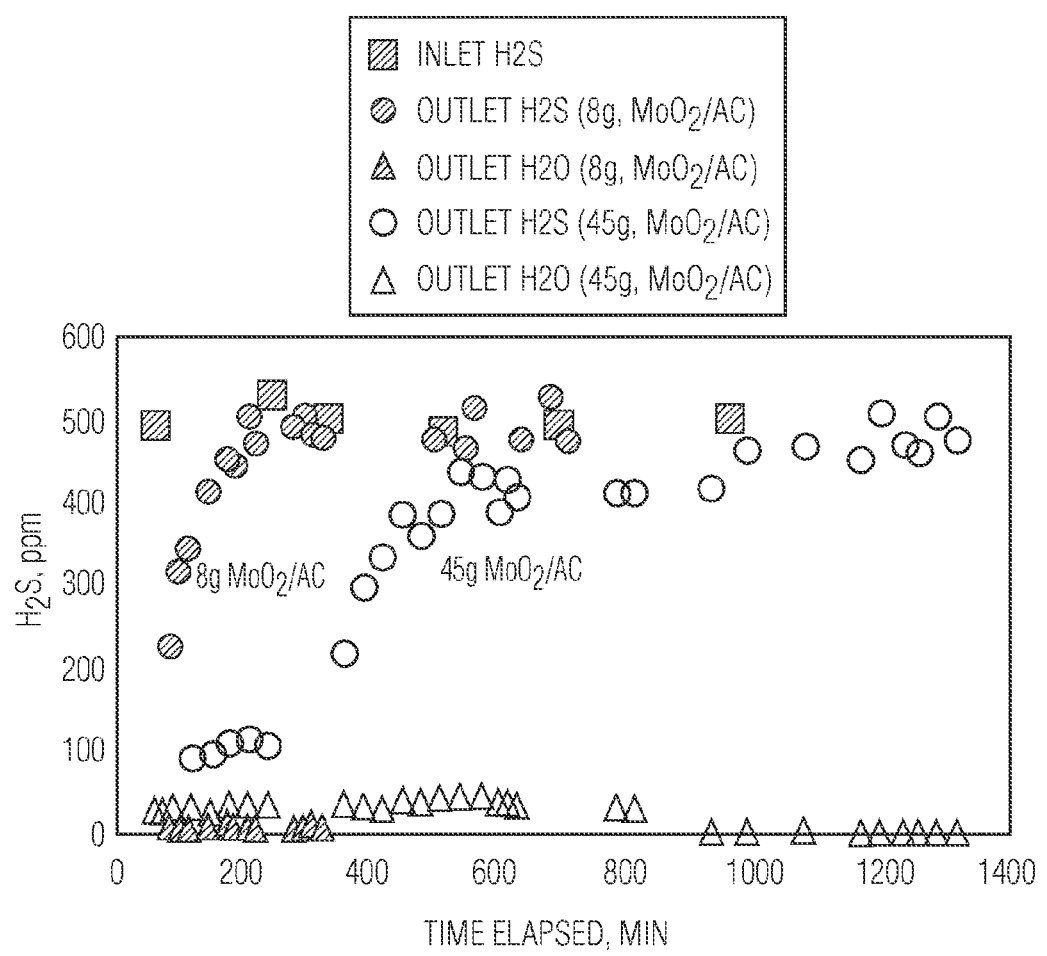
FIG. 3 is a graph plot of sulfidation breakthrough curves derived from data collected at different points during preparation of the catalyst composition in accordance with the present invention.

The sulfidation breakthrough curves when using 5% $H_2S$/$H_2$ as the sulfiding agent, are shown in FIG. 3 for two different batches: 8 grams and 45 grams of the calcined pellets. As the breakthrough curves indicate, rapid consumption of hydrogen sulfide was observed during the initial period of sulfidation, but this consumption slowly stabilized over time as the breakthrough curves begin to plateau. As the breakthrough curves further show, 8 grams of the calcined pellets require about 200 minutes for complete sulfidation, while 45 grams of the calcined pellets require about 1000 minutes for complete sulfidation.

Upon complete sulfidation, the resulting sulfidized pellets are purged with an inert gas (e.g., nitrogen) at 100 mL/min for about 0.5 hr to remove any physically adsorbed hydrogen sulfide, and then allowed to cool under an inert atmosphere of nitrogen gas to yield sulfidized pellets containing molybdenum sulfide. The resulting product is stored under an inert atmosphere to prevent undesirable oxidation and moisture uptake that would otherwise occur in the presence of ambient air. It is noted that the sulfidation/calcination reactor is preferably selected from a quartz tube reactor.

In step 20, the sulfidized pellets are impregnated with an aqueous solution of cesium formate using a solution feed rate of from about 4 to 12 mL/hr in a rotary evaporator to uniformly distribute the solution in the sulfidized pellets in a manner similar to a spray drying technique. Cesium formate was obtained and complied with CAS No. 3495-36-1. The amount of the cesium formate solution added is sufficient to achieve a cesium to molybdenum mass ratio of from about 0.5 to 3, and more preferably about 1 (a cesium to molybdenum molar ratio of about 0.7).

The impregnated pellets are vacuum-dried overnight at about 70° C. and stored in an inert atmosphere (e.g., nitrogen gas). It is noted that care must be taken to avoid exposure of cesium to ambient air as cesium can readily absorb oxygen from ambient and form undesirable cesium oxide species. The presence of such cesium oxide species can result in segregation of cesium in bulk phases on the active material and reduce catalyst activity for synthesizing alcohols. The resulting active material must be stored in an inert atmosphere (e.g., nitrogen purged bottles).

The present invention will now be described for synthesizing ethanol and higher alcohols. The following description by no means limits the scope and spirit of the present invention.

In another embodiment of the present invention, there is provided a method of synthesizing an alcohol from synthesis gas or syngas, including the steps of acquiring a catalyst composition comprising an active material having a molybdenum- and sulfur-containing substance impregnated with an effective amount of cesium sufficient to promote synthesis of an alcohol, carried on an inert support, wherein the active material is at least substantially free of a transition metal, and contacting a mixture of hydrogen and carbon monoxide to the catalyst composition under suitable conditions to yield an alcohol.

In a preferred embodiment of the present invention, the mixture of hydrogen/carbon monoxide is at least substantially free of sulfur-based compounds such as, for example, hydrogen sulfide. The mixture of hydrogen/carbon monoxide includes hydrogen to carbon monoxide volume ratio of at least 0.1, preferably from about 0.5 to 3, and more preferably about 1.

In one embodiment of the present invention, the present catalyst composition can be used to catalyze the conversion of hydrogen/carbon monoxide gas mixture to alcohols at a reaction temperature of from about 250° C. to 400° C., preferably at about 290° C. to 340° C., and under a pressure of from about 700 psig to 2000 psig, preferably at about 1000 psig to 1400 psig. In a preferred embodiment of the present invention, the mixture of hydrogen/carbon monoxide is passed through the catalyst composition at a gas hourly space velocity (GHSV) of from about 2000 L/kg catalyst/hr to 10000 L/kg catalyst/hr.

EXAMPLES

Example 1

Laboratory Catalyst Testing Unit Set Up

Figure 4:
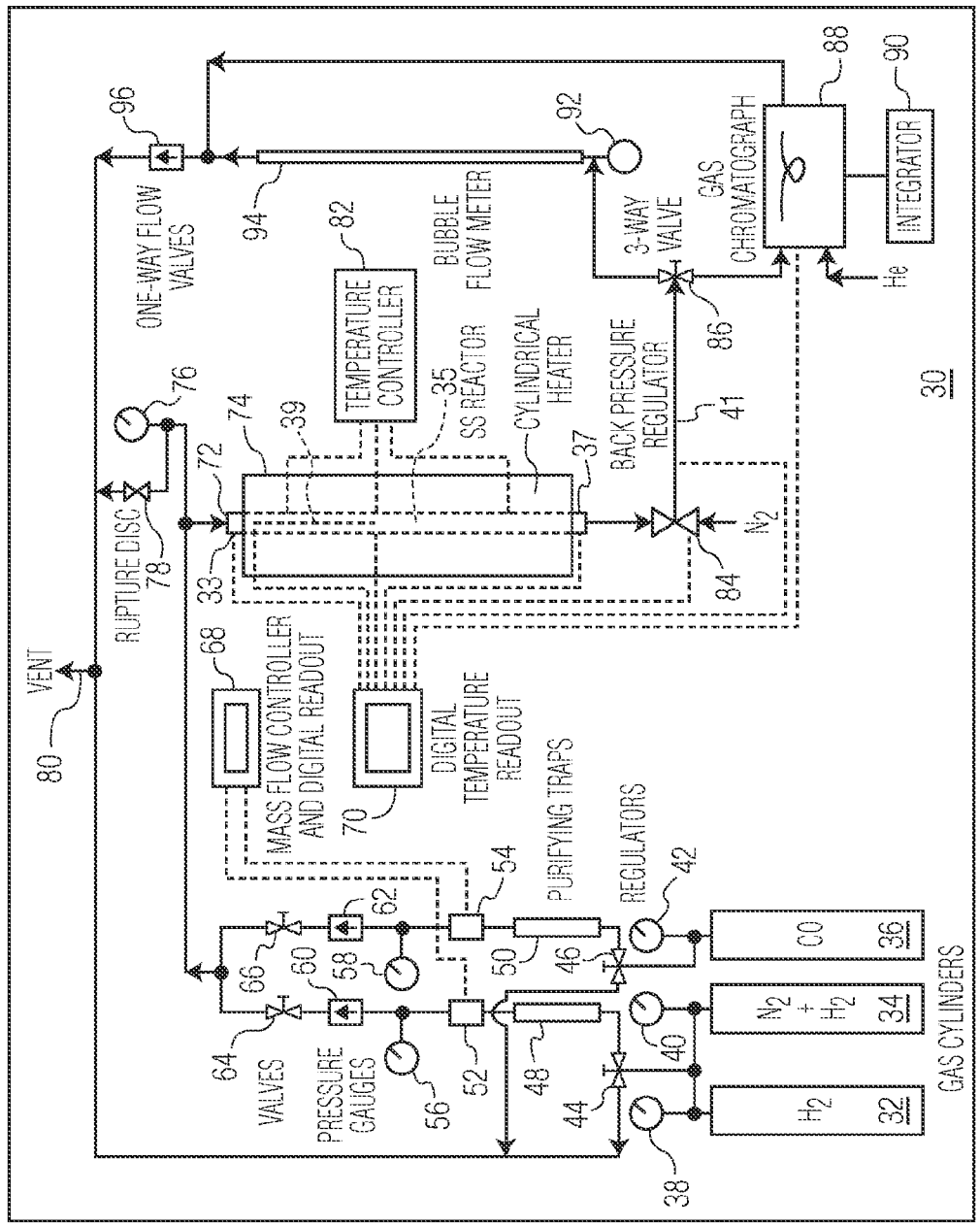
FIG. 4 is a schematic diagram of a laboratory testing unit used in analyzing the performance of the catalyst composition in accordance with the present invention.

A laboratory catalyst testing unit 30 as represented in the schematic diagram of FIG. 4 was used to initially test the present catalyst composition. The unit 30 is adapted for a typical maximum operating pressure of about 100 atm (1500 psig), and can be modified for pressures of up to about 125 atm (1800 psig). The unit 30 includes a plug flow reactor 72 in the form of a single pass fixed-bed tubular reactor for receiving and retaining the present catalyst composition in the form of a catalyst bed (not shown but described in Example 2 below).

The reactor 72 includes a stainless steel tubing (e.g., schedule 40, 316 stainless steel) having 1.27 cm ID (½" ID/¾" OD), and a stainless steel vertical thermo-well (0.32 cm OD) adapted for measuring the temperature of the catalyst in the reactor 72. The unit 30 includes a split tube furnace 74 positioned about the reactor 72 for supplying heat to the reactor 72. The split tube furnace 74 includes three separate heating zones, each individually controlled by a temperature controller 82 to regulate the catalyst bed temperature to within ±1° C.

The reactor 72 is configured to receive hydrogen, hydrogen/nitrogen, and/or carbon monoxide supplied from gas sources 32, 34, and 36, respectively. The gas sources 32, 34, and 36 include pressure regulators 38, 40 and 42, respectively, to monitor tank pressure and to regulate pressure of the corresponding supplied gas. Prior to reaching the reactor 72, the gases are initially passed through purifying traps 48 and 50 to trap moisture and other impurities that may be present, such as iron carbonyl from an old carbon monoxide tank.

The gas flow of each of the gases is monitored and regulated by respective mass flow controllers 52 and 54 integrated with a 4-channel controller unit 68. The mass flow controllers 52 and 54 are adapted to operate at high pressures, while regulating the hydrogen and carbon monoxide flows individually, and the 2% hydrogen/nitrogen gas at atmospheric pressure. The pressure of the gases is monitored by respective pressure gauges 56 and 58.

Valves 64 and 66 are provided to open and close passage of the gases into the reactor 72. One-way valves 60 and 62 are provided to prevent any reverse flows from the reactor 72. Valves 44 and 46 are used to occasionally depressurize reactant gases from inlet lines, which are released through vent 80. A back pressure regulator 84 located downstream from the reactor 72 ensures that the desired pressure in the reactor 72 is maintained via the gas sources 32, 34, and/or 36. The back pressure regulator 84 reduces the downstream pressure to atmospheric, while maintaining upstream pressure at the desired levels. Reactor pressure is monitored through a pressure gauge 76 located near the inlet of the reactor 72.

The inlet and outlet lines of the reactor 72 are wrapped in heating/insulating tapes to maintain temperatures at about 150° C. to 200° C. and prevent condensation of reaction product components within the unit 30. The temperatures were monitored via a temperature readout unit 70 at various points in the unit 30 including reactor inlet 33, reactor tube 35, reactor outlet 37, internal axial reactor area 39, back pressure regulator 84, line 41 downstream from the back pressure regulator 84, and the gas chromatograph 88.

The product stream from the reactor 72 can be directed either to the gas chromatograph 88 coupled to an integrator/printer 90 for performing analysis of the reaction productions or to a bubble meter 94 using a 3-way valve 86. The gas chromatograph 88 utilizes a Poroplot Q capillary column (12.5 m) equipped with a 6-way valve configured for injection of a portion of the heated outlet gas stream. The bubble meter 94 including a snoop solution reservoir 92 is adapted to measure reactor outlet flow rate. A one-way valve 96 is provided downstream from the bubble flow meter 94 and the gas chromatograph 88 to prevent any reverse flows from vent 80.

For safety purposes, CO and $H_2$ alarms were in continual use. A rupture disc 78 is provided for safety reasons. Bubble meter outlet, GC outlet and any purge gases from inlet lines were released via vent 80 and expelled through an exhaust hood.

In situ catalyst reduction of the present catalyst composition in the reactor 72 was carried out by passing 2% $H_2$/balance $N_2$ at 60 ml/min through the catalyst bed of the reactor 72 at atmospheric pressure. Over a period of about 2 hours, the temperature in the reactor 72 was gradually increased from ambient to a final reduction temperature of about 350° C. The reduction process was monitored by measuring the water content of the exiting gas through the gas chromatograph 88. The reduction process was complete upon detection of a sudden drop in the water content of the exiting gas.

Example 2

Performance of the Catalyst Composition of the Present Invention

A catalyst composition of the present invention having an active material, with a molybdenum content of about 10.6 wt % and a cesium content of about 9.9 wt %, carried on an inert support composed of activated carbon, was prepared in accordance with the present invention. The prepared catalyst composition was tested in the laboratory catalyst testing unit 30 of Example 1 at a temperature of 315° C. and pressure of 1406 psig using a syngas containing $H_2$/CO volume ratio of about 1.

A comparison of the results of the performance of the present catalyst composition with $MoS_2$-based catalysts reported recently in the literature is provided below in Table 1.

TABLE 1

| Catalyst | Composition (Mo/Co/Alkali) (wt %) | $H_2$/CO (v/v) | T, ° C. | P, Psig | GHSV, (L/L cat/hr) | GHSV, L/kg cat/hr) | CO Conv., (mol %) | Total Alcohols, (g/kg cat/hr) | Total Alcohols, (g/kg act mat/hr)* | $C_{2+}$ Alc./ MeOH (w/w) |
|---|---|---|---|---|---|---|---|---|---|---|
| Cs/$MoS_2$/AC (Present Invention) | 10.6/0/9.9 | 1.0 | 315 | 1406 | 6000 | 8000 | 12.3 | 281 | 1375 | 0.70 |
| $K_2CO_3$/CoS/$MoS_2$/AC[(1)] (Catalyst A) | 30.8/9.5/5.7 | 1.1 | 330 | 2400 | 4032 | 2626*** | 11.7 | 320 | 696 | 0.55 |
| $K_2CO_3$/Co/$MoS_2$/AC[(2)] (Catalyst B) | 13.6/2.7/9 | 1.0 | 325 | 1436 | 5353 | 4352 | 8.0 | 194 | 767 | 0.50 |
| $K_2CO_3$/$MoS_2$/CNT**[(3)] (Catalyst C) | 15/0/9 | 2.0 | 320 | 1385 | 2527*** | 3600 | 32.9 | 110 | 458 | 0.45 |

*"active material" is the total weight of elemental Mo, alkali (Cs or K) and/or Co present in the catalyst
**CNT = Multiwalled Carbon Nanotubes
***Calculated based on Catalyst composition
[(1)]Iranmahboob, et al., Catal, Letters, 78 (2002) 49.
[(2)]Christensen, et al., Appl. Catal. A, Gen., 366 (2009) 29.
[(3)]Surisetty, et al., Appl. Catal. A, Gen., 365 (2009) 243.

As shown in Table 1, the present catalyst composition exhibits improved catalyst performance over those observed in the prior art. Although Catalyst C is reported to exhibit high CO conversion, it possesses a low value of alcohol production indicating undesirable formation of high amounts of hydrocarbons.

Cobalt containing catalysts A and B have been reported to lose sulfur very quickly. The loss of sulfur adversely affects performance. For example, it has been reported that the production of total alcohols and $C_{2+}$ alcohols to methanol ratio of catalyst B decreases respectively from initial 1091 g/kg act mat/hr and 0.9 to 767 g/kg act mat/hr and 0.50 with increase in time on stream from 24 hr to 27.5 hr. Such catalysts typically require continuous replenishment of sulfur to maintain performance levels. This is generally accomplished by sustaining continuous sulfidation through addition of hydrogen sulfide in the syngas feedstock to make-up for the sulfur loss.

Unlike Catalysts A and B, the present catalyst composition does not require re-sulfidation.

Catalyst A has also been observed to produce over 5% water, while the present catalyst composition produces little or no water as a by-product. Production of water increases the energy consumption of the process as it necessitates energy intensive alcohols-water separation.

Example 3

Long Term Performance Results

Figure 5:
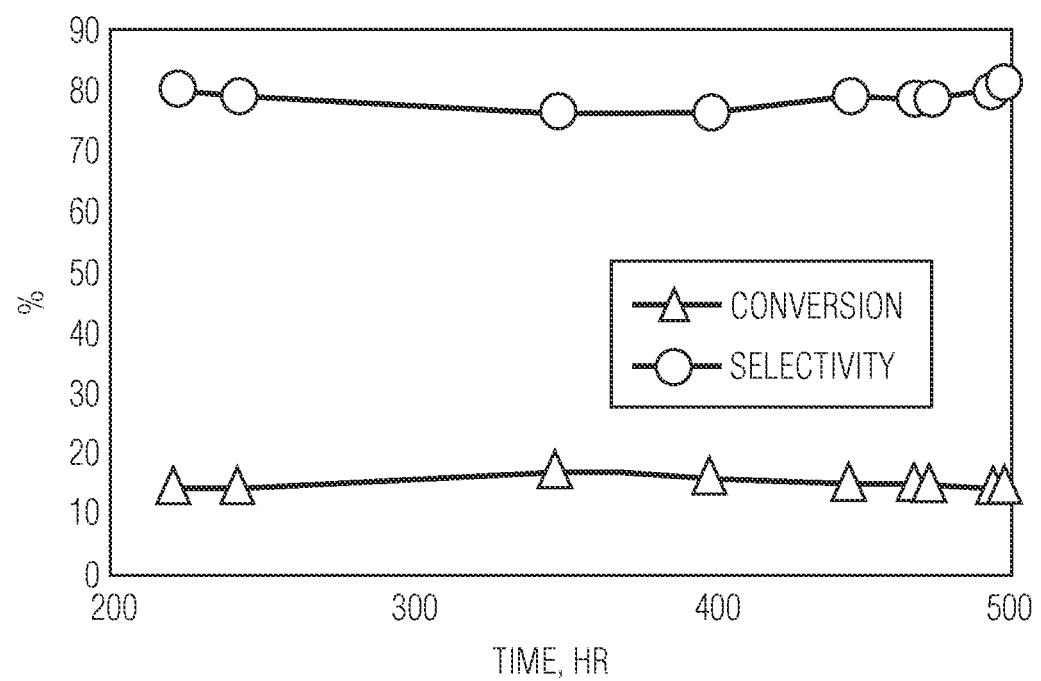
FIG. 5 is a graph plot of conversion and selectivity curves illustrating the stability of the catalyst composition during testing in accordance with the present invention.

In reference to FIG. 5, the present catalyst composition tested in Example 2 exhibited long term stability of over 500 hours of continuous operation. The carbon monoxide conversion and alcohols was observed to remain stable throughout the entire period of operation. No loss of sulfur was also observed during operation.

Example 4

Reproducibility of Catalyst Preparation

Figure 6:
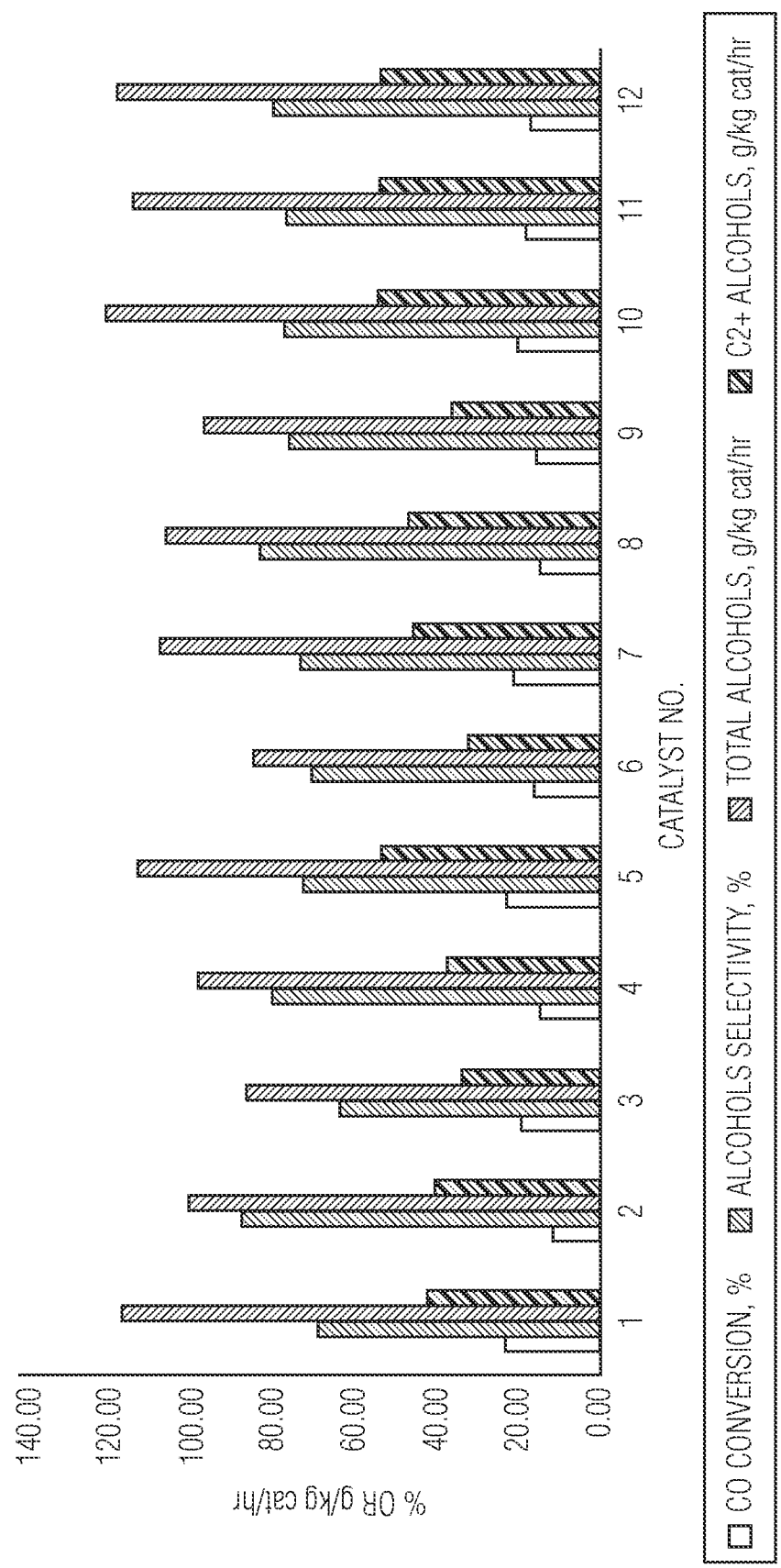
FIG. 6 is a graph plot detailing the activity and selectivity of different samples of the catalyst composition prepared in accordance with the present invention.

A graphical representation of carbon monoxide conversion, alcohols selectivity, total alcohols and $C_{2+}$ alcohol with catalyst batch numbers is shown in FIG. 6. The catalyst batch numbers represent present catalyst compositions prepared separately in different batches. As can be seen, the catalyst performance is fairly similar irrespective of the preparation batch. This indicates that the preparation method used in the present invention produces very consistent catalyst compositions.

Example 5

Results of Catalyst Performance at Higher Flow Rates

The catalyst composition of the present invention comprising $Cs/MoS_2/AC$ can be used at high synthesis gas flow rates, and at lower flow rates. Table 2 below shows steady-state results obtained with the laboratory testing unit of Example 1 after more than 24 hours with a gas hourly space velocity (GHSV) of from about 8000 L/kg catalyst/hr to 10000 L/kg catalyst/hr. In this example, a maximum alcohol production of 281 g/kg catalyst/hr with 85% selectivity to alcohols was obtained at GHSV of about 8000 L/kg catalyst/hr, 315° C., 1400 psig, and $H_2/CO=1$. Corresponding productions of ethanol and $C_{2+}$ alcohols were 100 g/kg catalyst/hr and 115 g/kg catalyst/hr, respectively.

It is noted that the CO conversion was observed to remain at a level where the exothermicity of the synthesis reactions did not lead to undesirable sintering of the present catalyst composition. It was also observed that the present catalyst composition can also be utilized with synthesis gas having a composition of $H_2/CO=2$.

TABLE 2

| Catalyst | $H_2$/CO, (v/v) | T, °C. | P, Psig | GHSV, L/kg cat/hr) | CO Conv., % | Alcohols Selectivity, % | Total Alcohols, g/kg cat/hr | $CO_2$, g/kg cat/hr | Methanol, g/kg cat/hr | Ethanol, g/kg cat/hr |
|---|---|---|---|---|---|---|---|---|---|---|
| 4 | 1 | 323 | 1486 | 10000 | 12.5 | 70.2 | 270.6 | 365.7 | 166.9 | 90.3 |
| 10 | 1 | 315 | 1406 | 8000 | 12.3 | 85.1 | 280.7 | 294.5 | 165.5 | 100.0 |
| 11 | 2 | 329 | 1228 | 10000 | 8.1 | 90.8 | 192.1 | 135.9 | 133.4 | 49.7 |
|  | 1 | 329 | 1230 | 10000 | 7.6 | 91.3 | 234.4 | 193.9 | 150.7 | 70.8 |

Example 6

Parameters of the Present Catalyst Composition Under Laboratory Testing Conditions The present catalyst composition was tested for steady state performance using the laboratory catalyst testing unit of Example 1. The present catalyst composition can be used under a wide range of reaction conditions. The stabilization time is the time period required for the present catalyst composition under reaction conditions to reach its steady-state level of activity and selectivity. Stability time is the time period under which the present catalyst composition was tested to verify that the catalyst did not undergo deactivation during its operation. A listing of reaction conditions and corresponding steady state results from the test is provided in Table 3 below.

TABLE 3

| Present Catalyst Composition | | Operating Conditions | | Steady-State results | |
|---|---|---|---|---|---|
| Active Material, wt % | 25-35 | Temp, °C. | 290-340 | Total Alcohols, g/kg cat/hr | 80-281 |
|  |  | Pressure, psig | 1000-1400 | Alcohols Selectivity, % | 70-90 |
| Cesium, wt % | 10-15 | GHSV, L/kg cat/hr | 2000-10000 | CO Conversion, % | 7-25 |
|  |  |  |  | Stabilization time, hr | 25-70 |
| Batch Size, g | 10-50 | $H_2$/CO, (v/v) | 1 | Stability time, hr | >500 |
|  |  |  |  | Ethanol/Methanol, w/w | 0.4-0.75 |
|  |  |  |  | $C_{2+}$/Methanol, w/w | 0.45-0.9 |

Example 7

Scaled-up Catalyst Testing Unit Set up

Figure 7:
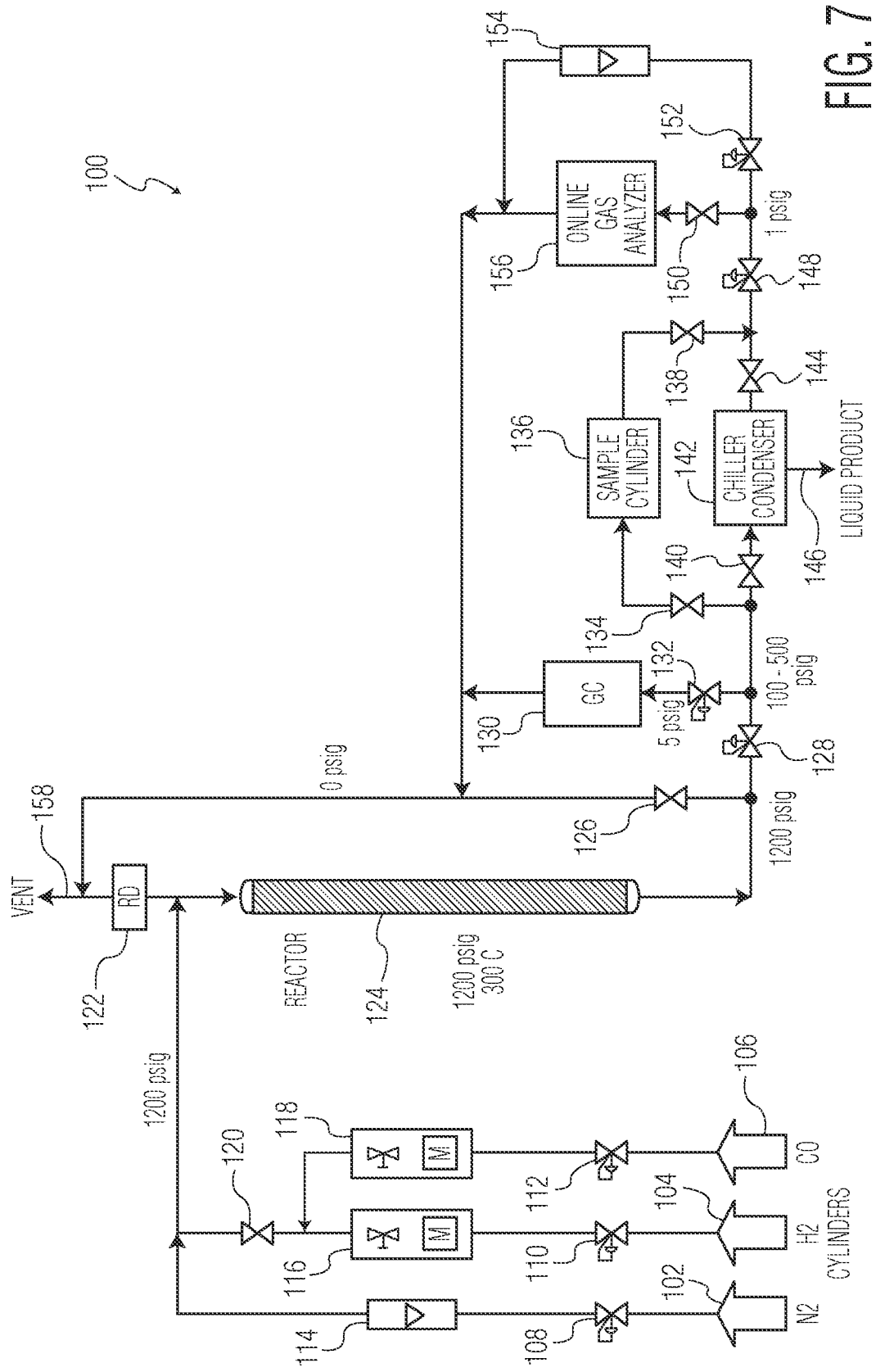
FIG. 7 is a schematic diagram of a scaled-up catalyst testing unit utilizing the catalyst composition in accordance with the present invention.

Referring to FIG. 7, a scaled-up catalyst testing unit 100 was constructed using a configuration similar to the lab scale catalyst testing unit 30 of Example 1. The unit 100 was constructed with a 0.834" ID×42" long stainless steel tube reactor 124, and a plurality of band heaters 222 to 229 (see FIG. 8) disposed therearound for heating the reactor 124. The reactor 124 is adapted to receive a gas stream containing hydrogen and carbon monoxide from gas sources 104 and 106, respectively, through corresponding pressure regulators 110 and 112.

The pressure regulators 110 and 112 were adjusted to maintain the downstream pressure at a desired reaction pressure. Integrated mass flow controllers 116 and 118 were used to control the flow of hydrogen and carbon monoxide in the gas stream into the reactor 124 at a desired molar ratio (hydrogen/carbon monoxide). A back pressure regulator 128 was provided at the outlet of the reactor 124 to maintain the reactor pressure, while reducing the downstream pressure to about 100 to 500 psig.

An online gas chromatograph 130 was provided to analyze the product stream exiting the outlet of the reactor 124 via pressure regulator 132. A heated traced line was used to inject the product stream to the chromatograph 130 through the regulator 132 to prevent condensation of alcohols.

Alternatively, the product stream was optionally passed through a chiller/condenser 142 via valves 140 to condense alcohols from the product stream. The condensed alcohols can thereafter be removed via outlet 146 as a liquid product. In this mode, valves 134 and 138 are maintained in a closed state, while valves 140 and 144 remain in an open state.

In a second alternative, the product stream was passed through a sample cylinder 136 to allow a sample of the product stream to be collected for external analysis. This allowed the product sample to be tested to confirm data collected using the online gas chromatograph 130. In this mode where the sample was collected in the cylinder 136, the chiller condenser 142 was bypassed via opening of the valves 134 and 138, and maintaining the valves 140 and 144 in the closed state.

The product stream exiting the sample cylinder 136 or the chiller condenser 142 were passed through a regulator 148 to further reduce the pressure to about 1 psig. An online gas analyzer 156 was provided for measuring carbon monoxide, hydrogen, methane and carbon dioxide as a small amount of the product stream passes via valve 150. The remaining product stream passes through regulator 152 to further reduce the pressure to atmospheric pressure and through a rotameter 154 to measure gas flow prior to its release via vent 158.

A rupture disk 122 and valve 126 were provided to safely and quickly vent the reactor 124 in the event of any unforeseen temperature excursion. During reactor shutdown, the unit 100 including the reactor 124 was purged with nitrogen from gas source 102 through regulator 108 and rotameter 144.

Figure 8:
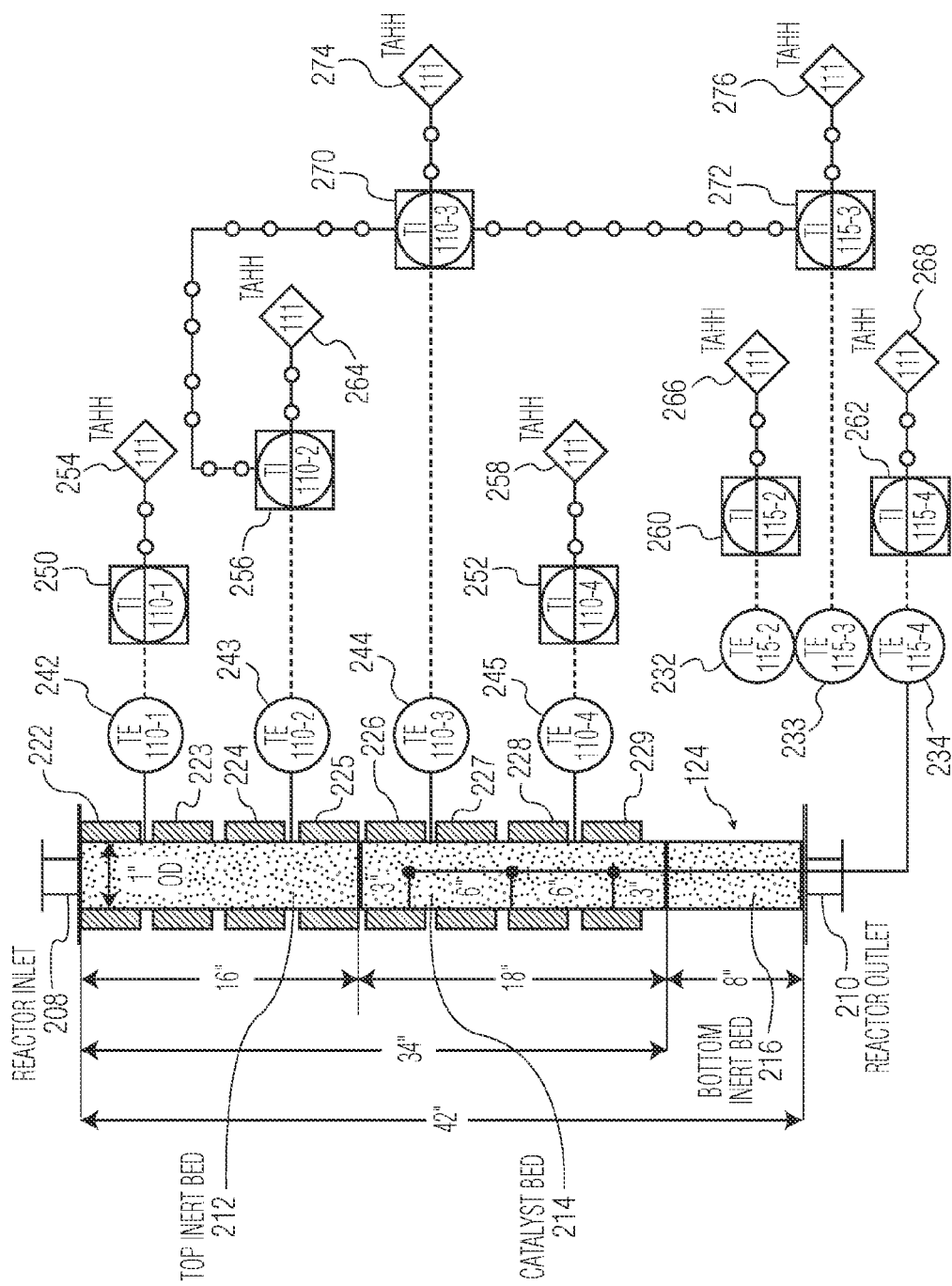
FIG. 8 is a schematic diagram of a reactor forming part of the scaled-up catalyst testing unit of FIG. 7 in accordance with the present invention.

Referring to FIG. 8, the reactor 124 includes a top inert bed 212 located near the reactor inlet 208, a bottom inert bed 216 located near the reactor outlet 210 and a catalyst bed 214 located therebetween. The top inert bed 212 was composed of an inert material selected from pyrex glass beads, glass helices, glass raschig rings, or the like, and measured about 16 inches long. The bottom inert bed 216 was composed of an inert material selected from pyrex glass beads, glass helices, glass raschig rings, or the like, and measured about 8 inches.

The catalyst bed 214 composed of the present catalyst composition in an amount of about 100 grams, measured about 18 inches. The reactor 124 further included eight band heaters 222 to 229, which are each configured for supplying heat uniformly to the top inert bed 212 and the catalyst bed 214 to achieve a desired temperature therein. The band heaters 222 to 225 are used to heat the top inert bed 212 in order to preheat the reactant gases (i.e., hydrogen and carbon monoxide) before reaching the catalyst bed 214. The remaining band headers 226 to 229 are used to regulate the reaction temperature of the catalyst bed 214.

The heat input supplied by the band heaters 222 to 229 was readily determined through temperature measurements of the external reactor walls via corresponding temperature sensors 243 and 244 located at the top inert bed 212 and the catalyst bed 214, respectively. Temperature sensors 242 and 245 are configured to measure reactor wall temperatures in the top inert bed 212 and catalyst bed 214, respectively. Temperature sensors 242 and 245 were appropriately positioned to measure reactor wall temperatures in the top inert bed 212 and catalyst bed 214, respectively.

Internal temperatures within the catalyst bed 214 were monitored at three location using thermocouples 232, 233 and 234. The three thermocouples 232, 233, and 234 were operatively associated on a probe. The thermocouple 232 was positioned within the catalyst bed 214 about 3 inches from the top inert bed 212. The thermocouple 233 was positioned within the catalyst bed 214 about 6 inches from the thermocouple 232. The thermocouple 234 was positioned within the catalyst bed 214 about 12 inches from the thermocouple 232.

Due to concerns of potential runaway reaction, a complex reactor temperature control system was installed. All temperature measurements were continuously monitored, recorded and controlled. For example, the temperature measured by the elements 232 and 234 were continuously displayed on a computer monitor via temperature indicators 260 and 262. The temperature indicators 260 and 262 provided signal to alarm monitors 266 and 268 respectively. The monitors 266 and 268 were set to a certain maximum temperature. In the event the temperature exceeds this value, the reactor operation was set to shut down immediately. The temperature measured by temperature elements 233, 244 and 243 were used to control the heat input to the reactor using corresponding temperature controllers 272, 270 and 256.

The temperature controllers 272, 270 and 256 were set to provide signal to alarm monitors 276, 274 and 264, respectively, which were programmed to generate an alarm signal a certain maximum temperature. In the event, the temperature exceeds this value, the reactor operation was set to shut down immediately. Similarly temperature measured by elements 245 and 242 was indicated by temperature indicators 252 and 250, respectively, and provided signals to the alarm monitors 258 and 254, respectively, which were set to shut the reactor down if the temperature exceeded the set point temperature.

Example 8

Samples of the Present Catalyst Composition as Tested in Scaled-up Catalyst Testing Unit A batch of 145 g of the present catalyst composition (Cs/MoS$_2$/AC) was prepared in three different batches (catalysts designated as Nos. 11, 12 and 13) and mixed together for the testing. A 100 g charge of the present catalyst composition was loaded into the reactor 124 (see FIGS. 7 and 8) and reduced in H$_2$/N$_2$ atmosphere as described previously above.

The details of the present catalyst compositions are listed in Table 4 below. Table 4

TABLE 4

| Catalyst Nos. | Batch Size, Gm | Active Material, wt % | Cs, wt % |
|---|---|---|---|
| 11 | 50 | 29.38 | 15.68 |
| 12 | 50 | 28.95 | 13.57 |
| 13 | 45 | 28.66 | 14.19 |

The temperature of the catalyst bed 214 was controlled at three different locations to obtain a uniform catalyst bed temperature. Copper lining was incorporated at the outside surface of the reactor 124 to facilitate uniform distribution of heat from band heaters 222 to 229. A temperature difference within 15° C. was obtained using this technique. The chiller/condenser 142 in the form of a double pipe heat exchanger was maintained at about −20° C. A 75 ml separator (cylinder) connected to the chiller/condenser 142 was maintained at room temperature under a pressure of from about 500 psig to 600 psig, and used to collect the liquid product.

Gaseous product was collected in a sample cylinder 136 pressurized at the reaction pressure. Gaseous and liquid product samples collected were subsequently analyzed using GC. Series of syringe injections were made from the collected samples to obtain the product compositions. The liquid product was clear in appearance and no other components were present in the liquid other than alcohols and minimal traces of water.

Reaction Conditions

The reaction conditions employed include pressures in the range of from about 1200 psig to 1300 psig and temperatures in the range of from about 325° C. to 330° C. The reactions are highly exothermic and can potentially create a run-away situation if the temperatures are not controlled. As described above, the reactor 124 was configured with an extensive temperature control arrangement.

Example 9

Test Results of the Present Catalyst Composition

As described above in Example 8, a larger scale testing of the present catalyst composition was carried out in the scaled-up catalyst testing unit 100 of Example 7 which comprised a 0.834" ID and 42" long stainless steel tube reactor 124. The reactor 124 was heated by external band heaters 222 to 229 to maintain constant temperatures inside the reactor 124. About 145 g of the present catalyst composition ($Cs/MoS_2/AC$) were prepared from three different batches (designated at catalysts Nos. 11 to 13) and then mixed together for the testing. A 100 g catalyst charge was loaded and reduced in 2% $H_2/N_2$ atmosphere.

The test results are shown in Table 5 below.

TABLE 5

|  | Lab Reactor Unit | Scaled Up Reactor Unit |
|---|---|---|
| Operating Conditions |  |  |
| Catalyst Weight, g | 3 | 100 |
| Temperature, C. | 328 | 326 (avg.) |
| Press, psig | 1230 | 1220 |
| $H_2$/CO | 1 | 1 |
| GHSV, l/kg cat/hr | 3000 | 3000 |
| Products, g/kg cat/hr |  |  |
| Alcohols | 123.7 | 106.0 |
| $CH_4$ | 38.6 | 13.8 |
| $CO_2$ | 210.1 | 96.0 |
| $H_2O$ | Trace | Trace |

Higher alcohols to methanol ratios of from about 0.91 w/w to 1.11 w/w (0.58 mol/mol to 0.71 mol/mol) and ethanol to methanol ratios of from about 0.62 w/w to 0.78 w/w (0.43 mol/mol to 0.54 mol/mol) were obtained in both cases. It is important to note that while the alcohols production is reasonably similar between both reactors 72 and 124, respectively, the amounts of $CH_4$ and $CO_2$ produced as by-products were observed to be significantly less in the larger test reactor. Also, the present catalyst composition did not produce water as a by-product. This is an important feature because separation of water from alcohol is generally an energy intensive process.

The forgoing discussion discloses and describes merely exemplary embodiments of the present invention. One skilled in the art will readily recognize from such discussion, and from the accompanying claims, that various changes, modifications, and variations can be made therein without departing from the spirit and scope of the invention as defined in the following claims.

What is claimed is:

1. A catalyst composition comprising an active material having a molybdenum- and sulfur-containing substance impregnated with an effective amount of cesium sufficient to promote synthesis of an alcohol, carried on an inert activated carbon support, wherein said active material is free of physically adsorbed hydrogen sulfide, and transition metals, other than molybdenum.

2. The catalyst composition of claim 1, wherein the molybdenum- and sulfur containing substance is molybdenum sulfide.

3. The catalyst composition of claim 1, wherein the cesium to molybdenum mass ratio is in the range of from 0.1 to 3.

4. The catalyst composition of claim 3, wherein the cesium to molybdenum mass ratio is in the range of from about 0.5 to 3.

5. The catalyst composition of claim 4, wherein the cesium to molybdenum mass ratio is about 1.

6. The catalyst composition of claim 1, wherein the effective amount of cesium is at least 0.1 wt %, based on the total weight of the composition.

7. The catalyst composition of claim 6, wherein the effective amount of cesium is from about 2 wt % to 30 wt %, based on the total weight of the composition.

8. The catalyst composition of claim 7, wherein the effective amount of cesium is from about 10 wt % to 15 wt %, based on the total weight of the composition.

9. The catalyst composition of claim 1, wherein the molybdenum- and sulfur containing compound and cesium is present in an amount of from about 5 wt % to 70 wt %, based on the total weight of the composition.

10. The catalyst composition of claim 9, wherein the molybdenum- and sulfur containing compound and cesium is present in an amount of from about 25 wt % to 35 wt %, based on the total weight of the composition.

11. A method of preparing a catalyst composition, comprising the steps of:

forming crystalline molybdenum oxide carried on an inert activated carbon support from a molybdenum oxide precursor via thermal decomposition;

reacting crystalline molybdenum oxide with hydrogen sulfide, by passing hydrogen sulfide in contact with the crystalline molybdenum oxide at a reaction temperature for a sufficient time to sulfidize the crystalline molybdenum oxide and yield molybdenum sulfide wherein said molybdenum sulfide is free of transition metals, other than molybdenum;

removing any hydrogen sulfide physically adsorbed on the molybdenum sulfide; and distributing cesium uniformly through said molybdenum- and sulfur-containing substance.

12. The method of claim 11, wherein the molybdenum oxide precursor is ammonium molybdate tetrahydrate.

13. The method of claim 11, wherein the crystalline molybdenum oxide forming step further comprises:

impregnating said inert activated carbon support with said molybdenum oxide precursor; and calcining the precursor for a sufficient time to yield the crystalline molybdenum oxide.

14. The method of claim 13, wherein the impregnation step comprises applying a solution of the molybdenum oxide precursor to the inert activated carbon support via rotary evaporation.

15. The method of claim 14, wherein the molybdenum oxide precursor solution is applied in an amount sufficient to achieve a molybdenum loading of from about 10 wt % to 18 wt % based on the total weight of the impregnated inert activated carbon support.

16. The method of claim 13, wherein the molybdenum oxide precursor is calcined at from about 400° C. to 550° C.

17. The method of claim 13, further comprising washing the inert activated carbon support with an acid prior to the impregnating step.

18. The method of claim 17, wherein the acid is selected from the group consisting of nitric acid, acetic acid, formic acid, sulfuric acid, and combinations thereof.

19. The method of claim 18, wherein:
the acid is nitric acid.

20. The method of claim 11, wherein the cesium distributing step comprises:

applying a solution of a cesium-containing compound to the molybdenum- and sulfur-containing substance via rotary evaporation; and drying said molybdenum- and sulfur-containing substance under an inert atmosphere.

21. The method of claim 20, wherein the cesium-containing compound solution is applied in an amount sufficient to achieve a cesium to molybdenum mass ratio in the range of from 0.1 to 3.

22. The method of claim 21, wherein the cesium to molybdenum mass ratio is in the range of from about 0.5 to 3.

23. The method of claim 22, wherein the cesium to molybdenum mass ratio is about 1.

24. The method of claim 20, wherein the cesium-containing compound is cesium formate.

25. A method of synthesizing an alcohol from synthesis gas or syngas, comprising the steps of:

acquiring a catalyst composition comprising an active material having a molybdenum- and sulfur-containing substance impregnated with an effective amount of cesium sufficient to promote synthesis of an alcohol, carried on an inert activated carbon support, wherein said active material is free of physically adsorbed hydrogen sulfide, and transition metals, other than molybdenum; and contacting syngas to the catalyst composition under suitable conditions to yield an alcohol.

26. The method of claim 25, wherein the suitable conditions comprises a reaction temperature of from about 250° C. to 400° C. and under a pressure of from about 700 psig to 2000 psig.

27. The method of claim 26, wherein:
the reaction temperature is from about 290° C. to 340° C.; and
the pressure is from about 1000 psig to 1400 psig.

28. The method of claim 25, wherein the contacting step comprises flowing the syngas at a gas hourly space velocity of from about 2000 L/kg catalyst/hr to 10000 L/kg catalyst/hr.

29. The method of claim 25, wherein the syngas is free of sulfur.

30. The method of claim 25, wherein the syngas comprises a hydrogen to carbon monoxide volume ratio in the range of from 0.1 to 3.

31. The method of claim 30, wherein the hydrogen to carbon monoxide volume ratio is from about 0.5 to 3.

32. The method of claim 31, wherein the hydrogen to carbon monoxide volume ratio is about 1.

33. The method of claim 25, wherein the molybdenum- and sulfur-containing substance is molybdenum sulfide.

34. The method of claim 25, wherein the cesium to molybdenum mass ratio is at least 0.1.

35. The method of claim 34, wherein the cesium to molybdenum mass ratio is in the range of from about 0.5 to 3.

36. The method of claim 35, wherein the cesium to molybdenum mass ratio is about 1.

37. The method of claim 25, wherein the effective amount of cesium is at least 0.1 wt %, based on the total weight of the composition.

38. The method of claim 37, wherein the effective amount of cesium is from about 2 wt % to 30 wt %, based on the total weight of the composition.

39. The method of claim 38, wherein the effective amount of cesium is from about 10 wt % to 15 wt %, based on the total weight of the composition.

40. The method of claim 25, wherein the active material is present in an amount of from about 5 wt % to 70 wt %, based on the total weight of the composition.

41. The method of claim 25, wherein the active material is present in an amount of from about 25 wt % to 35 wt %, based on the total weight of the composition.

42. The method of claim 25, further comprising an alcohol synthesis in the range of from about 80 g/kg catalyst/hr to 281 g/kg catalyst/hr.

43. The method of claim 25, further comprising an alcohols selectivity of at least 70%.

44. The method of claim 43, wherein the alcohols selectivity is in the range of from about 70% to 90%.

45. The method of claim 25, further comprising a carbon monoxide conversion of at least 7%.

46. The method of claim 45, wherein the carbon monoxide conversion is in the range of from about 7% to 25%.

47. The method of claim 25, wherein the alcohol is a mixture of ethanol and methanol, and the alcohol mixture is synthesized at an ethanol to methanol weight ratio of from about 0.4 to 0.75.

48. The method of claim 25, wherein the alcohol is a mixture of ethanol, higher alcohols and methanol, and the alcohol mixture is synthesized at an ethanol/higher alcohols to methanol weight ratio of from about 0.45 to 0.9.

49. The method of claim 25, wherein said catalyst composition undergoes no loss of sulfur during alcohol synthesis.

50. The method of claim 25, wherein said catalyst composition forms trace amounts of water during alcohol synthesis.

* * * * *